(12) United States Patent
van Groningen et al.

(10) Patent No.: US 8,181,778 B1
(45) Date of Patent: May 22, 2012

(54) PACKAGE WITH CATHETER

(75) Inventors: David van Groningen, Zelhem (NL); Ad van Velthoven, Beusichem (NL)

(73) Assignees: Cure Medical Ltd., Santa Maria, CA (US); Integral Medical Products Co., Ltd., Zhejiang (CN)

( * ) Notice: Subject to any disclaimer, the term of this patent is extended or adjusted under 35 U.S.C. 154(b) by 0 days.

(21) Appl. No.: 13/010,487

(22) Filed: Jan. 20, 2011

(51) Int. Cl.
 *B65D 83/10* (2006.01)
 *B65D 81/24* (2006.01)
 *A61B 19/02* (2006.01)
 *A61L 2/00* (2006.01)

(52) U.S. Cl. .......................... 206/364; 206/210; 422/28

(58) Field of Classification Search ................. 206/210, 206/364; 422/28; 604/171, 172, 265, 544
See application file for complete search history.

(56) References Cited

U.S. PATENT DOCUMENTS

| | | | | |
|---|---|---|---|---|
| 5,147,341 | A * | 9/1992 | Starke et al. | 604/349 |
| 6,578,709 | B1 * | 6/2003 | Kavanagh et al. | 206/364 |
| 6,602,244 | B2 * | 8/2003 | Kavanagh et al. | 604/544 |
| 7,380,658 | B2 * | 6/2008 | Murray et al. | 206/364 |
| 7,766,163 | B2 * | 8/2010 | Tanghoej | 206/364 |
| 8,011,505 | B2 * | 9/2011 | Murray et al. | 206/364 |
| 2008/0023346 | A1 * | 1/2008 | Vonderwalde | 206/210 |
| 2008/0260576 | A1 * | 10/2008 | Bruun et al. | 422/28 |
| 2009/0131917 | A1 * | 5/2009 | Kavanagh et al. | 604/544 |

* cited by examiner

*Primary Examiner* — Bryon Gehman
(74) *Attorney, Agent, or Firm* — Sherr & Vaughn, PLLC

(57) ABSTRACT

Package for a catheter, with a catheter having catheter tube with a distal end and a proximal end, the proximal end being provided with a catheter connector. A main body is provided for holding the catheter, and a cap for closing off the main body. A gel container is positioned inside the main body, the gel container being provided with a cavity for holding an amount of a lubricating agent. The gel container includes a first opening at a distal end thereof, and a second opening at a proximal end thereof.

19 Claims, 3 Drawing Sheets

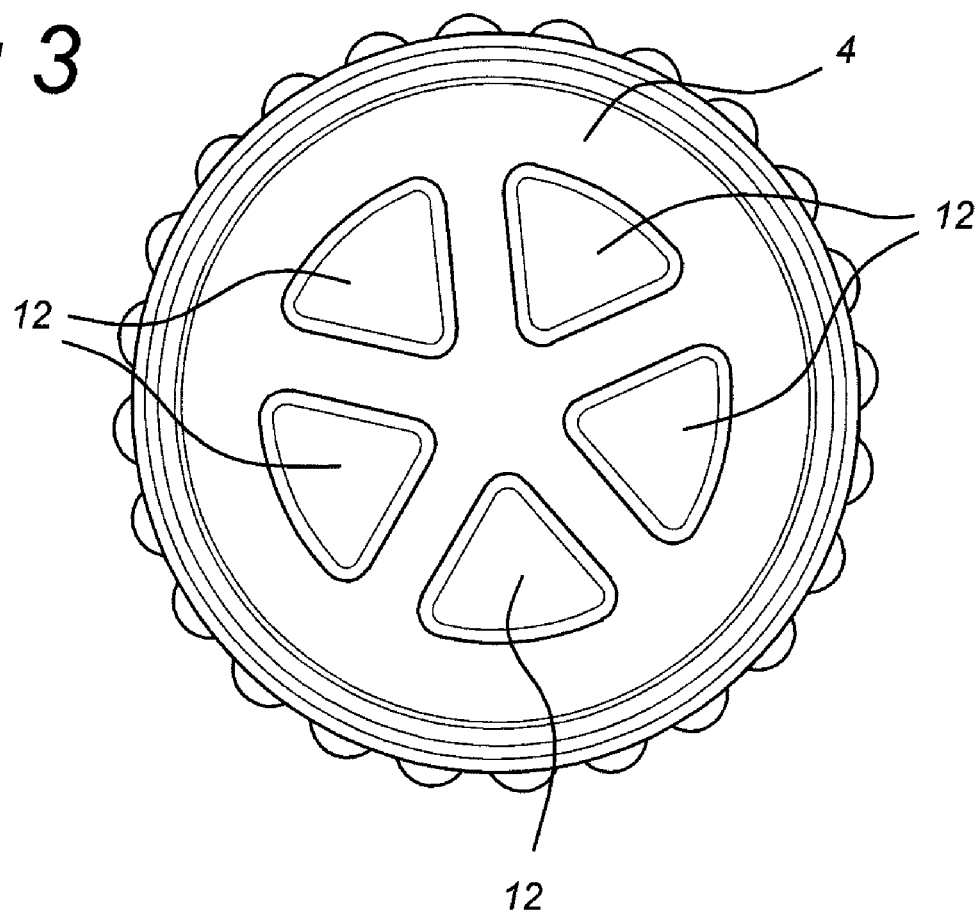

PACKAGE WITH CATHETER

CROSS REFERENCE TO RELATED APPLICATIONS

The present application claims priority under 35 U.S.C. §119 to European Patent Application No. 10189987.0 (filed on Nov. 4, 2010), which is hereby incorporated by reference in its entirety.

FIELD OF THE INVENTION

Embodiments of the present invention relates to a package with a catheter, e.g., a urethral catheter, which can be used for (intermittent) self-catheterization by a patient.

BACKGROUND OF THE INVENTION

International patent publication WO00/47494 discloses a storage package with a catheter. The catheter is provided with a coated surface, which exhibits a reduced friction when wetted with a wetting liquid. The wetting liquid is provided in the storage package, and thus contacts the coated surface during the entire shelf live.

British patent application GB-A-2 319 507 discloses a packaged catheter with a lubricant activating liquid. In the package which comprises the catheter, also a container with a liquid (water) is provided. Prior to actual use, the container may be opened such that the liquid can activate the coating on the catheter.

SUMMARY OF THE INVENTION

Embodiments of the present invention seeks to provide an enhanced package for a (urethral) catheter, suitable for every day use by a patient.

In accordance with embodiments of the present invention, a package is provided for a catheter that includes at least the following: a catheter having a catheter tube with a distal end and a proximal end, the proximal end being provided with a catheter connector; a main body for holding the catheter; a cap for closing off the main body, and a gel container positioned inside the main body, the gel container being provided with a cavity for holding an amount of gel-like lubricating agent, and including a first opening at a distal end, and a second opening at a proximal end, the first opening diameter corresponding to a catheter diameter, and the second opening diameter being larger than the catheter diameter.

In accordance with embodiments of the present invention, the catheter can be applicable, for example, as a urethral catheter, which may be used by the patient or a physician. Embodiments of the present invention allows an equal and easy spread of the lubricating agent when opening the package and taking out the catheter, while having an easy to use and easy to store package. This makes the package according to the present invention suitable for intermittent self-catheterization.

In accordance with embodiments of the present invention, the main body includes a first part for receiving the cap, a second part for holding the gel container and a third part for holding a distal end of the catheter, in which the first part has an inner diameter which is less than an inner diameter of the second part, and the third part has an inner diameter which is less than the inner diameter of the second part. This allows to sufficiently seal off the package allowing it to be carried by a person before actual use.

The third part of the main body is arranged to hold the catheter tube in a space which is shorter than the length of the catheter tube. This variant would allow packaging of longer catheters, e.g. urethral catheters for men.

In accordance with embodiments of the present invention, the gel container can include locking members extending beyond the inner diameter of the first part. This allows to lock the gel container in place inside the package in a simple and reliable manner.

In accordance with embodiments of the present invention, the gel container can include an inner sealing member (e.g., in the form of a ring) at the second opening, which in co-operation with the catheter (e.g., the connector part of the catheter) seals off the gel container. In a further variant, the catheter may comprise a closing member (e.g., as part of the connector) for sealing of the second opening of the gel container when positioned in the main body. This sealing member aids in preventing lubricating agent from escaping from the package before actual use of the catheter.

In accordance with embodiments of the present invention, the outside dimensions of the package are congruent with the catheter. In other words, a first part of the package (where the connector is located) has an outside diameter smaller than an outside diameter of a second part (where the catheter tube is located). By following the shape of the catheter, a package may be provided with minimal dimensions, making it easy to carry and to store.

In accordance with embodiments of the present invention, the length of the package corresponds to the length of the catheter. This again makes possible a package with minimal dimensions, and allows quick identification of the catheter present in the package.

In accordance with embodiments of the present invention, the lubricating agent can include a gel, thereby allowing easy assembly of the package.

In accordance with embodiments of the present invention, in order to make the catheter suitable for application by the major part of patients, the catheter can be made of a material without a softening agent, e.g., PVC with a nelaton tip.

In accordance with embodiments of the present invention, the cap can be made of a transparent material. This allows to have codes on the catheter (or on the catheter connector) to be visible while the package is still closed off. The codes may be dimension codes, application codes, etc.

In accordance with embodiments of the present invention, the cap can be provided with one or more openings, and optionally with a filter element (such as a paper filter). This allows to sterilize the package and its contents after assembly, by gas sterilization.

In accordance with embodiments of the present invention, a method for sterilizing a package can include at least one of the following: assembling a main body, a gel container, a catheter and a cap having one or more openings, and then sterilizing internal elements of the package by introducing a sterilizing gas through the one or more openings in the cap. This is a very efficient and cost-effective manner of sterilizing the package and its contents in a sufficient manner.

BRIEF DESCRIPTION OF THE DRAWINGS

Embodiments of the present invention will be discussed in more detail below, using a number of exemplary embodiments, with reference to the attached drawings.

Example

Example

Example

Example

Example FIG. 3 illustrates a top view of a cap of the package of example FIG. 1, in accordance with embodiments of the present invention.

DETAILED DESCRIPTION OF EMBODIMENTS

Embodiments of the present invention aim to provide an easy to use and easy to carry solution for providing a medical device in the form of a catheter. As an example, the medical device is a urethral catheter allowing to empty the bladder of a patient. Embodiments of the present invention provide for a package in which catheter 1 such as a urethral catheter can be carried, which is ready for use when taken from the package. Urethral catheter 1 may be used for intermittent self-catheterization.

Figure 1:
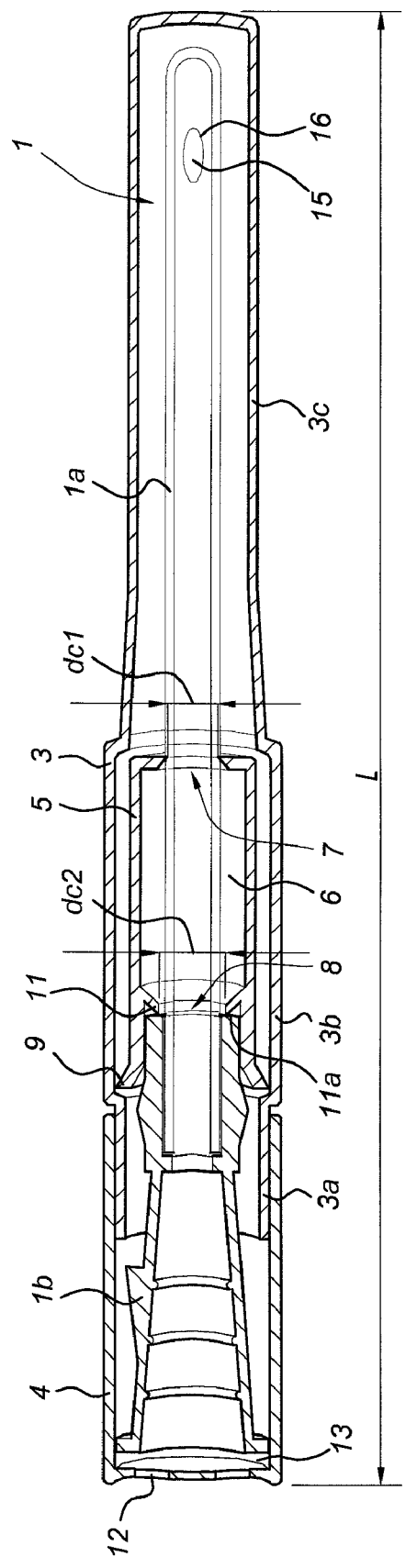
FIG. 1 illustrates a cross sectional view of a package, in accordance with embodiments of the present invention.

Example FIG. 1 illustrates a cross sectional view of an exemplary embodiment of the present invention, showing all elements is assembled state.

As illustrated in example FIG. 1, catheter 1 includes main body 3 which is closed off at a distal end thereof, and which can be closed of at a proximal, open end using cap 4. The cap 4 can be attached to the main body 3 using various attachment/locking methods, such as a screw thread, a bayonet closure or a clamping arrangement.

Figure 2A:
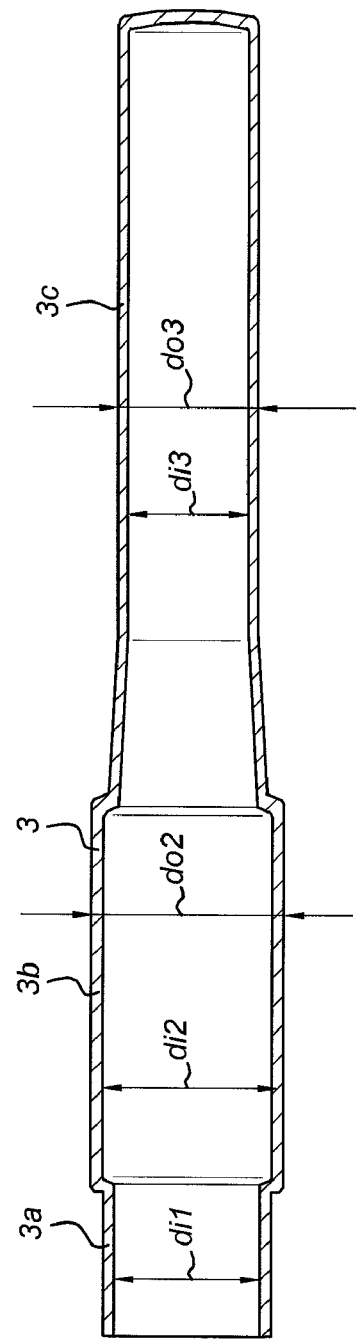
FIG. 2a illustrates a cross sectional view of a main body of the package of example FIG. 1, in accordance with embodiments of the present invention.

Example FIG. 2a illustrates a cross sectional view of main body 3, which is divided into first part 3a, second part 3b and third part 3c, which have first internal diameter $di_1$, second internal diameter $di_2$ and third internal diameter $di_3$, respectively. First part 3a is arranged for receiving cap 4, second part 3b for holding gel container 5 and third part 3c for holding catheter tube 1a of catheter 1. In accordance with embodiments, first part 3a has first inner diameter $di_1$ which is less than second inner diameter $di_2$ of second part 3b. Third part 3c has third inner diameter $di_3$ which is less than second inner diameter $di_2$ of second part 3b.

Cap 4 may have a dimension which allows cap 4 to cover the entire outer surface of first part 3a, thus providing a pen-like appearance for the package. In accordance with embodiments, cap 4 is made of a transparent material, which allows inspection of connector 1b of catheter 1 (which can, e.g., shows size or other indicia, markings, etc. on connector 1b).

As illustrated in example FIGS. 1 and 2a, outer diameter $do_3$ of third part 3c may have a transition part from second part 3b. The outside dimensions of the package are congruent with the general form of catheter 1, or follows the general dimensions of catheter 1, i.e. package 10 can have a long, pen-shaped geometric shape. In more general terms, a first part of package 10 has an outside diameter less than an outside diameter of a second part (i.e., outer diameter $do_3$ of third part 3c of main body 3 is less than outside diameter $do_2$ of second part 3b, as illustrated in example FIG. 2a).

Figure 2B:
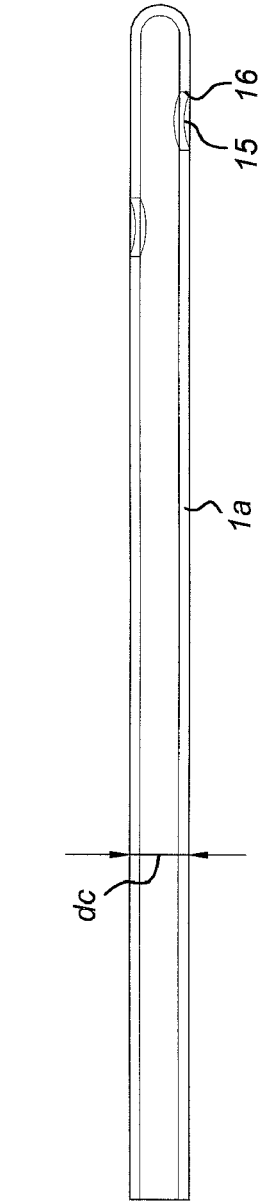
FIG. 2b illustrates a cross sectional view of a catheter of the package of example FIG. 1, in accordance with embodiments of the present invention.

As illustrated in example FIG. 2b, catheter 1 such as a urethral catheter is provided and can be stored in main body 3. Catheter 1 includes a distal end in the form of catheter tube 1a provided with a rounded end and one or more discharge openings 15. Openings 15 are provided with rounded and or polished rims 16, such that the entry of urethral catheter tube 1a into the urethral tract of a patient is as comfortable as possible for the patient. At a proximal end thereof, catheter 1 is provided with catheter connector 1b, which may be used to attach catheter 1 to a collection bag or other collection device. The dimensions of package 10 (or more specifically, the internal dimensions of main body 3 and cap 4) are adapted to allow storage of the entire catheter 1 (which may have varying dimensions). In accordance with embodiments, catheter 1 can have a length in a range of between about 10-15 cm, which makes catheter 1 especially suited for use with female patients.

As illustrated in example FIG. 1, in accordance with embodiments, length L of package corresponds to the length of catheter 1. In essence, length L of package is slightly greater than the length of catheter 1 so that the package surrounds the entire catheter 1.

In accordance with embodiments, urethral catheter 1 is made of a plastic material without any softening agent. Such a material thereby prevents possible sensitivity issues with the patient. The plastic material may, for example, be a PVC type of material. Catheter tube 1a may be provided with a nelaton tip.

Figure 2C:
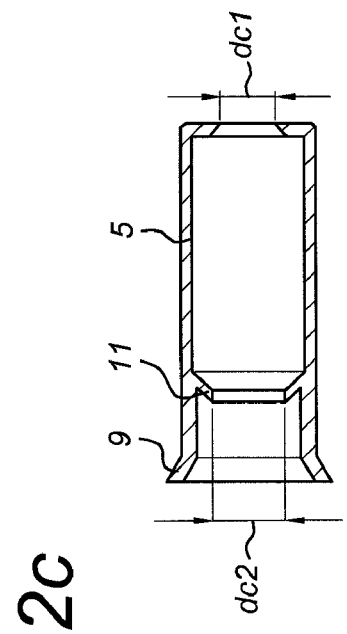
FIG. 2c illustrates a cross sectional view of a gel container of the package of example FIG. 1, in accordance with embodiments of the present invention.

Furthermore, gel container 5 is provided and positioned in second part 3b of main body 3 as illustrated in the cross-sectional view of example FIG. 1. As illustrated in example FIG. 2c, gel container 5 is illustrated as a single element. Gel container 5 is provided with cavity 6, in which an amount of a gel-like lubricant agent is stored. Gel container 5 includes first opening 7 at a distal end thereof, and second opening 8 at a proximal end thereof. First opening 7 has diameter $dc_1$ corresponding generally to outer diameter dc of catheter tube 1a. Second opening 8 has diameter $dc_2$ being greater than outer diameter dc of catheter tube 1a. This allows to provide a layer of the gel-like lubricant on the outside surface of the entire catheter 1 when taking or otherwise removing catheter 1 out of the package, thereby making catheter 1 ready for instantaneous use. First opening 7 may be provided as a skewed surface in the material of gel container 5, with diameter $dc_1$ that is less than outer diameter dc of catheter tube 1a, the flexible material thereby providing a good seal interface at first opening 7 and the outer wall of catheter tube 1a.

In accordance with embodiments, the lubricating agent includes a gel-like material. Alternatively, additional components may be included in the lubricating agent, such as compositions having a medicinal function.

Gel container 5 is held in position in main body 3 by matching the dimensions of gel container 5 to second inner diameter $di_2$ of second part 3b. Gel container 5 is provided with one or more locking members 9, which extend beyond first inner diameter $di_1$ of first part 3a. During manufacturing, gel container 5 can be forced-fit into position in second part 3b of main body 3, and locking members 9 assure a proper fixation of gel container 5. Locking members 9 are, e.g., extensions of the material of gel container 5, or a ring like extension of flexible material. Gel container 5 is e.g. made of a soft material, such as silicone.

As illustrated in example FIG. 1, in accordance with embodiments, gel container 5 includes inner sealing member 11 at second opening 8, which in co-operation with catheter 1 (e.g., via the end part 11a of connector 1b) seals off gel container 4. Also, inner sealing member 11 provides a constant thickness film on the outer surface of catheter tube 1a when catheter 1 is taken out of the package.

In accordance with embodiments, catheter 1 can alternatively include a closing member, e.g., as part of connector 1b, for sealing off second opening 8 of gel container 5 when catheter 1 is positioned in main body 3.

In accordance with embodiments, third part 3c of main body 3 can alternatively be arranged to hold catheter tube 1b of catheter 1 in a space which is less than the length of catheter tube 1b, e.g., in a folded or coiled up manner. This would also allow to use the present invention package embodiments for longer urethral catheters, e.g., intended for use by male patients.

In order to permit the package and catheter 1 to be used by patients themselves, catheter 1 is sterilized when assembling the package with catheter 1. As illustrated in example FIG. 1, in accordance with embodiments, cap 4 of the package can alternatively be provided with one or more openings 12. Openings 12 are sealed off with filter element 13, e.g. in the form of a paper element. After assembling main body 3, gel container 5, catheter 1 and cap 4, the internal elements of the package (i.e., the inner lumen of main body 3 and catheter 1) by introducing (e.g., injecting) a sterilizing gas through the one or more openings in cap 4.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A catheter package comprising:
   a main body defining a first annular cavity;
   a cap provided at a proximal end of the main body which closes off a proximal end of the main body, the cap having a plurality of openings configured to permit the introduction of a sterilizing gas into the catheter package;
   a catheter received in the first annular cavity of the main body, the catheter including a catheter tube having an distal end thereof which is distal with respect to the cap;
   a catheter connector provided at a proximal end of the catheter tube; and
   a gel container extending through the first annular cavity of the main body, the gel container defining a second annular cavity sized to receive and hold a lubricating agent, the gel container comprising a first opening at a distal end thereof, and a second opening at a proximal end thereof, the first opening having an inner diameter which is approximately the same as an outer diameter of the catheter tube, and the second opening having an inner diameter which is greater than the outer diameter of the catheter tube.

2. The catheter package of claim 1, wherein the main body comprises:
   a first section adapted to be received by the cap;
   a second section adapted to receive the gel container; and
   a third section adapted to receive a distal end of the catheter tube.

3. The catheter package of claim 2, wherein:
   the first section has an inner diameter which is less than an inner diameter of the second section; and
   the third section has an inner diameter which is less than the inner diameter of the second section.

4. The catheter package of claim 2, wherein the third section of the main body has a length which is less than the length of the catheter tube.

5. The catheter package of claim 2, wherein the gel container comprises locking members having an outer circumferential region which overlaps an inner circumferential region of the first section.

6. The catheter package of claim 1, wherein the gel container comprises an inner sealing member at the second opening, said inner sealing member forming a seal at an interface between the gel container and a distal end of the catheter connector.

7. The catheter package of claim 1, wherein the outside dimensions of the catheter package are congruent with the catheter tube.

8. The catheter package of claim 1, wherein the length of the package corresponds to the length of the catheter tube.

9. The catheter package of claim 1, wherein the lubricating agent comprises a gel.

10. The catheter package of claim 1, wherein the catheter tube is made of a material that does not include a softening agent.

11. The catheter package of claim 1, wherein the cap is made of a transparent material.

12. A catheter package comprising:
    a main body which is open at a proximal end thereof and closed off at a distal end thereof;
    a gel container extending through and received in the main body, the gel container being sized to receive and hold a lubricating agent therein;
    a catheter connector extending partially through the gel container and from the main body;
    a catheter tube received in the main body and partially in the catheter connecter and the gel container; and
    a cap which closes off the proximal end of the main body, the cap having at least one opening at a proximal end thereof and a filter provided at the proximal end adjacent the at least one opening,
    wherein the main body comprises a first section which extends into the cap, a second section through which the gel container extends, and a third section through which the catheter tube partially extends.

13. The catheter package of claim 12, wherein the gel container includes a first opening at a distal end thereof and having a first diameter, and a second opening at a proximal end thereof and a second diameter which is greater than the first diameter.

14. The catheter package of claim 12, wherein:
    the first section has an inner diameter which is less than an inner diameter of the second section; and
    the third section has an inner diameter which is less than the inner diameter of the second section.

15. The catheter package of claim 12, wherein the gel container comprises:
    a locking member which flares outwardly from a proximal end of the gel container to abut the inner surface of the main body at a transition between the first section and the second section when the gel container is received by the catheter tube; and
    a sealing member which flares inwardly from the inner surface of the gel container to form a seal at an interface between the gel container and the catheter connector.

16. The catheter package of claim 12, wherein the catheter tube comprises discharge openings.

17. The catheter package of claim 12, wherein the catheter tube is made of a material that does not include a softening agent.

18. The catheter package of claim 12, wherein the cap is made of a transparent material.

19. A method of sterilizing a catheter package, the method comprising:

assembling the catheter package comprising:
- a main body which is open at a proximal end thereof and closed off at a distal end thereof;
- a gel container extending through and received in the main body, the gel container being sized to receive and hold a lubricating agent therein;
- a catheter connector extending partially through the gel container and from the main body;
- a catheter tube received in the main body and partially in the catheter connecter and the gel container; and
- a cap which closes off the proximal end of the main body, the cap having a plurality of openings at a proximal end thereof and a filter provided at the proximal end adjacent the plurality of openings, wherein the main body comprises a first section which extends into the cap, a second section through which the gel container extends, and a third section through which the catheter tube partially extends; and then sterilizing internal elements of the catheter package by introducing a sterilizing gas through the plurality of openings in the cap.

* * * * *